(12) United States Patent
Colman et al.

(10) Patent No.: US 9,675,773 B2
(45) Date of Patent: Jun. 13, 2017

(54) AIRWAY TUBE

(75) Inventors: Joshua Lewis Colman, Jerusalem (IL); Gershon Levitsky, Jerusalem (IL)

(73) Assignee: ORIDION MEDICAL (1987) LTD., Jerusalem (IL)

( * ) Notice: Subject to any disclaimer, the term of this patent is extended or adjusted under 35 U.S.C. 154(b) by 486 days.

(21) Appl. No.: 12/679,529

(22) PCT Filed: Sep. 25, 2007

(86) PCT No.: PCT/IL2007/001189
§ 371 (c)(1),
(2), (4) Date: Apr. 7, 2010

(87) PCT Pub. No.: WO2009/040783
PCT Pub. Date: Apr. 2, 2009

(65) Prior Publication Data
US 2010/0204603 A1    Aug. 12, 2010

(51) Int. Cl.
*A61B 5/02* (2006.01)
*A61M 16/08* (2006.01)
*A61B 5/097* (2006.01)

(52) U.S. Cl.
CPC ......... *A61M 16/0816* (2013.01); *A61B 5/097* (2013.01); *A61M 16/085* (2014.02); *A61M 2230/432* (2013.01)

(58) Field of Classification Search
CPC . A61B 3/1241; A61B 5/14451; A61B 5/1495; A61B 5/14551; A61B 5/02154; A61B 5/1464; A61B 5/1459; A61B 5/14542; A61B 5/14552; A61B 5/097; A61N 1/36557

USPC ......................................................... 600/543
See application file for complete search history.

(56) References Cited

U.S. PATENT DOCUMENTS

| | | | |
|---|---|---|---|
| 2,693,800 A * | 11/1954 | Caldwell | 128/207.18 |
| 4,197,857 A | 4/1980 | Osborn | |
| 4,278,082 A * | 7/1981 | Blackmer | 128/207.18 |
| 4,932,269 A * | 6/1990 | Cammarata, III | A61B 5/087 |
| | | | 128/204.23 |
| 5,033,312 A | 7/1991 | Stupecky | |
| 5,347,843 A | 9/1994 | Orr | |
| 5,379,650 A | 1/1995 | Kofoed | |
| 5,595,174 A * | 1/1997 | Gwaltney | 128/201.15 |
| 5,765,558 A * | 6/1998 | Psaros et al. | 128/207.14 |
| 5,857,461 A * | 1/1999 | Levitsky et al. | 128/207.14 |
| 6,926,005 B1 * | 8/2005 | Colman | A61M 16/08 |
| | | | 128/202.27 |
| 2004/0206907 A1 * | 10/2004 | Yamamori et al. | 250/343 |

(Continued)

OTHER PUBLICATIONS

AARC Clinical Practice Guideline, Capnography/Capnometry during Mechanical Ventilation—2003 Revision and Update, Respiratory Care, 48(5):534-539 (May 2003).

(Continued)

*Primary Examiner* — Patricia Mallari
*Assistant Examiner* — Vasuda Ramachandran
(74) *Attorney, Agent, or Firm* — Fletcher Yoder, P.C.

(57) ABSTRACT

There is provided an airway tube for breath sampling, comprising a breath sampling port comprising two or more inlets adapted to sample breath from the airway tube. The inlets are connected to each other through a junction located outside of the air passageway of the airway tube.

12 Claims, 5 Drawing Sheets

(56) References Cited

U.S. PATENT DOCUMENTS

2007/0272247 A1* 11/2007 Porat ..................... 128/206.28
2008/0060657 A1* 3/2008 McAuley et al. ....... 128/207.18

OTHER PUBLICATIONS

International Search Report of PCT/IL2007/001189 dated May 26, 2008.
International Preliminary Report on Patentability of PCT/IL2007/001189 dated Jul. 7, 2008.

* cited by examiner

AIRWAY TUBE

RELATED APPLICATION DATA

This application is the U.S. National Stage of PCT/IL2007/001189 filed Sep. 25, 2007, the contents of which are herein incorporated by reference for all purposes.

FIELD

The invention relates to field of breath sampling devices.

BACKGROUND

Common practice in the medical field is the continuous measuring and analysis of carbon dioxide concentrations in exhaled breath of mechanically ventilated patients, anaesthetized patients, and patients suffering from particular forms of respiratory disease. Generally known as "Capnography", in medical practice Capnography is typically used to obtain information about a patient's physiological condition and/or physical condition. Some examples of these applications may include: to evaluate patient's end-tidal carbon dioxide; to monitor severity of pulmonary disease; to corroborate that tracheal intubation and not esophageal intubation has been performed; to continuously monitor proper operation of ventilation equipment; and, to measure volume of carbon dioxide elimination to assess metabolic rate and/or alveolar ventilation. More information on Capnography may be found in "AARC Clinical Practice Guideline, Capnography/Capnometry during Mechanical Ventilation—2003 Revision and Update", and Respiratory Care, May 2003, VOL 48, No. 5, all of which are hereby incorporated by reference.

Two methods are commonly used in the practice of Capnography, mainstream Capnography and side-stream Capnography. Both methods comprise the use of an appropriate breath sampler adapted to measure and analyze carbon dioxide samples in the patient's exhaled breath. The breath samplers generally employ technology based on, for example, infrared spectrography, molecular correlation spectrography, mass spectrography, Raman spectrography, or photo-acoustic spectrography, for the performance of the measurements and analyses.

In a mainstream Capnography system the breath sampler is directly coupled, through an appropriate adapter, to a patient airway tube connecting the patient to a ventilation machine. A sensor is inserted into the airway tube so that the exhaled breath passes directly over the sensor which measures the carbon dioxide concentration in the exhaled breath. The method is generally used with intubated patients as, for non-intubated patients, a mask is usually required which may be uncomfortable for patients in respiratory distress. In a side-stream Capnography system a breath sampler continuously draws samples of exhaled breath from the attached patient airway tube connecting the patient to the ventilation machine. Typically, a narrow diameter, flexible breath sampling tube extends from the breath sampler to the patient airway tube. Connection to the airway tube is typically by means of an airway adapter, which is a tube adapted to be connected to the patient airway tube (for example a tube exiting from a ventilator source) at one end, and through appropriate fittings, to the patient's intubation tube at the other end. Optionally, the airway adapter may be connected to a separate section of the patient airway tube at each end. Connection of the breath sampling tube to the airway adapter is usually performed through a sampling port in the airway adapter. The sampling port typically comprises a narrow bore tube, also referred to as "air collector", perpendicularly extending at one end towards the central axis of the airway adapter tube. At the other end, the air collector generally extends outwardly through a wall of the airway adapter tube to connect, by means of appropriate sampling port connection fittings, to the breath sampling tube. The air collector may include one or more relatively short extensions, referred to hereinafter as "inlets", generally perpendicularly extending from the air collector. The inlet comprises an aperture which is connected through a narrow bore to the bore of the air collector.

At the other end of the breath sampling tube is usually connected the breath sampler. The breath sampler is typically adapted with a pump which operates to continuously create a pressure drop along the path from the airway adapter to the breath sampler. By creating the pressure drop, which may also be referred to as "negative pressure differential", exhaled breath samples are continuously drawn from the airway adapter through the aperture(s) into the sampling port and thereon through the breath sampling tube to the breath sampler. The accuracy in the measurement and analysis of the breath samples is dependent on the samples experiencing a continuous, smooth, laminar flow when traveling from the patient to the breath sampler, such that the carbon dioxide waveform arriving at the breath sampler is substantially the same as that in the patient airway tube.

Techniques are commonly utilized in side-stream Capnography systems to try to prevent liquids, which tend to accumulate in the patient airway tube, from entering the breath sampling tube. These liquids may include, for example, liquids related to patient secretions, such as for example, mucous, condensed-out liquids resulting from high humidity in the ventilation means, and medications and saline solutions provided to a patient during lavage, suction and nebulization procedures. Entry of the liquids into the breath sampling tube may cause partial or total blockage in the tube, interfering with the flow of the breath samples and affecting the carbon dioxide measurement and analysis. Furthermore, liquids entering the breath sampler may cause damage to the device.

Entry of liquids into the breath sampling tube is generally through the sampling port in the airway adapter. Typically, these liquids reach the sampling port as a result of any one or combination of the following conditions:

a) Directly during patient coughing.
b) During lavage procedures wherein liquids (generally a saline solution) are injected into the patient airway towards the lungs to break down thick secretions. These procedures are typically performed prior to suctioning and cleaning the patient airway tube and may result in the liquids reaching the airway adapter if not synchronized well with inhalation.
c) During movement of the patient airway tubing as a result of moving the patient or direct movement of the tubing itself. Liquids collecting along the patient airway tube may then flow into the airway adapter and consequently reach the sampling port.
d) When the airway adapter is the lowest point in the patient airway, liquids may collect at the bottom of the airway and, if not emptied periodically, they may reach the sampling port. Furthermore, when air or exhaled breath flow in their respective directions inside the patient airway tube during the inhalation/exhalation cycle, the liquids may splash across the apertures in the sampling port and enter into the sampling port.

Liquids reaching the sampling port are drawn in through the aperture in the inlet or air collector as a result of the pressure drop between the airway adapter and the sampling port. This condition may cause a blockage in the sampling port. Despite the blockage, generally the pump in the breath sampler continues to work for a period of time increasing the pressure drop between the point of the blockage and the breath sampler. The increase in the pressure drop typically results in the liquid being pulled into the sampling port and subsequently into the breath sampling tube. Eventually, the increasing pressure drop reaches a threshold value at which the pump is inactivated, but usually not before the liquid has caused a blockage in the sampling port and/or the breath sampling tube.

Numerous types of airway adapters and sampling ports used in the art are adapted with filtering systems for the prevention of liquids from entering the breath sampling line. Generally, there are drawbacks with such adapters and/or sampling ports as described below.

An airway adapter comprises a sampling port wherein the sampling port comprises a metal filter made of sintered metal powder. The liquids are blocked by the metal filter from entering into the sampling port and into the breath sampling tube. A problem with this sampling port is that the metal filter is quickly covered with liquids, requiring frequent replacement of the filter.

A different airway adapter comprises a hydrophobic baffle lining the interior circumference of the adapter along a portion of its length. An exit port extends from the baffle and connects to a breath sampling tube, the hydrophobic baffle permitting the passage of the breath samples. A disadvantage in this airway adapter is that the baffle quickly fills up with liquid interrupting the smooth flow of the breath samples, thereby requiring frequent replacement of the airway adapter.

Another airway adapter comprises a sampling port with multiple inlets extending from an air collector. The inlets are adapted to independently permit the breath samples to flow through without any substantial waveform distortion should an aperture be blocked in one of the inlets. Additionally, the blockage is not pulled into the air collector as the open inlet(s) prevents an increase in the pressure drop between the sampling port and the breath sampler due to the blockage. A drawback with this sampling port is that the blocking liquid has a tendency to migrate from one aperture to another as a result of air and exhaled breath flow in opposite directions during the inhalation/exhalation cycle. Furthermore, the proximity between the inlets, the reduced surface area between the inlets and the corners at the base of the inlets provide additional surface tension area for the liquids to attach to as they migrate. These conditions may contribute to blocking of all apertures and liquids entering the sampling port, requiring replacement of the airway adapter.

As discussed above, airway adapters and/or sampling ports known in the art are not generally well adapted to serve as a "first line of defense" against liquids found in a medical environment associated with the use of ventilation equipment. These adapters and/or sampling ports have a tendency to suffer from blockages which generally require their frequent replacement. Furthermore, in some cases, they are designed with filters which prevent liquids from flowing into the sampling port but at the expense of degradation in the waveform of the exhaled breath samples.

There is therefore a need for an airway adapter and/or sampling port capable of handling exposure to liquids generally encountered in medical environments associated with patient ventilation. The airway adapter and/or sampling port should be adapted to prevent the entry of liquids into the breath sampling tube without interfering with or substantially altering the waveform of exhaled breath samples.

SUMMARY

An aspect of some embodiments of the invention relates to providing an airway tube comprising a breath sampling port, wherein the breath sampling port is adapted to sample exhaled breath from the airway tube, and wherein the entry of liquid into the breath sampling port is substantially restricted. Optionally, the airway tube may be an airway adapter.

According to an aspect of some embodiments of the invention, the breath sampling port comprises a plurality of inlets, each inlet adapted to sample breath samples from the airway tube. The inlets are physically separated from one another by sections of a circular inner wall of the airway tube, the sections referred to as "migration path". Occasionally, liquid inside the airway tube creates a blockage in a first inlet and crosses the migration path to an adjacent second inlet also creating a blockage in the second inlet. By providing a migration path with surface area substantially greater than the surface area of the second inlet the increased surface tension in the liquid substantially prevents the liquid from reaching the second inlet. As a result, blockage in the second inlet is prevented and breath sampling continued.

Additionally, according to an aspect of some embodiments of the invention, the breath sampling port comprises a junction to which the inlets are connected through a channel, and an air collector connecting the channel with a breath sampling tube. The inlets, channel and air collector comprise bores adapted to allow breath samples to flow through with substantially minimal effect on the waveform of the samples. The inlet lengths are substantially greater than the inlet bore diameter. The separation between two adjacent inlets is equal to or greater than the inlet lengths. Yet, the lengths of the inlets and the channel are kept relatively short so as to maintain a substantially small pressure drop between the aperture and the air collector, reducing the possibility that liquid blocking an aperture will be drawn into the inlet. Liquid drawn into the inlet may subsequently be drawn into the junction, air collector and/or the breath sampling tube, possibly creating a system blockage. As a result, by reducing the possibility of liquid entering the inlet, the probability of liquid blocking the whole system is substantially reduced.

In an embodiment of the invention, the breath sampling port is positioned such that the junction is externally located to the airway tube abutting an outer wall of the tube. The inlets, of equal lengths, extend into the airway tube from the same direction, or optionally, from different directions. Alternatively, the inlets are of different lengths. In another embodiment of the invention, the breath sampling port is positioned such that the junction is embedded between the outer wall and an inner wall of the airway tube. The inlets, of equal lengths, extend into the airway tube. Optionally, the inlet lengths are different. Alternatively, the junction is partially embedded in between the outer wall and inner wall. In yet another embodiment of the invention, the breath sampling port comprises inlets with an end section comprising a bore of substantially smaller diameter relative to the inlet bore diameter. The small bore diameter of the end section, which comprises an aperture also with a small diameter, enhances the hydrophobic, or water repelling, characteristics of the inlets.

In accordance with some embodiments of the invention there is provided an airway tube for breath sampling, comprising a breath sampling port comprising two or more inlets adapted to sample breath from the airway tube. The inlets are connected to each other through a junction located outside of the air passageway of the airway tube. In some embodiments of the invention, the junction is located outside of the outer wall of the airway tube. Optionally, the junction is located between the inner wall and the outer wall of the airway tube. Alternatively, the junction is at least partially located outside of the outer wall of the airway tube. Additionally or alternatively, the junction is at least partially located between the inner wall and the outer wall of the airway tube. For example, when a liquid droplet reaches one inlet and climbs towards the airway tube, such as the airway adapter, it reaches the airway tube's inner wall prior to reaching the second inlet. This prevents or at least reduces the passage of liquid from one inlet to another and thus, if and when one inlet is blocked by liquid the other inlet will remain open for airflow.

In accordance with some embodiments of the invention, there is provided an airway tube for breath sampling, comprising a breath sampling port comprising two or more inlets adapted to sample breath from the airway tube. The inlets are connected to each other through a junction located outside of the air passageway of the airway tube. The airway tube comprises an airway adapter.

In accordance with some embodiments of the invention, there is provided an airway tube for breath sampling, comprising a breath sampling port comprising two or more inlets adapted to sample breath from the airway tube. The inlets are connected to each other through a junction located outside of the air passageway of the airway tube. In some embodiments of the invention, a length of the inlet is substantially greater than a width of an aperture of the inlet. Additionally, the length of the inlet is shorter than a distance between two apertures of two adjacent inlets. Alternatively, the length of the inlet is substantially equal to the distance between two apertures of two adjacent inlets. Optionally, the inlet is narrowest at its respective aperture.

In some embodiments of the invention, one of the inlets has a length different from the other inlet. Additionally or alternatively, one of the inlets has the aperture oriented in a different direction from the aperture of the other inlet. Optionally, at least one of the inlets enters the airway tube from a direction different from the direction from which the other inlet enters the airway tube.

In accordance with some embodiments of the invention, there is provided a breath sampling port comprising two or more inlets adapted to sample breath from an airway tube. The inlets are connected to each other through a junction located outside of the air passageway of the airway tube. In some embodiments of the invention, a length of the inlet is substantially greater than a width of an aperture of the inlet. Additionally, the length of the inlet is shorter than a distance between two apertures of two adjacent inlets. Alternatively, the length of the inlet is substantially equal to the distance between two apertures of two adjacent inlets. Optionally, the inlet is narrowest at its respective aperture. In some embodiments of the invention, the inlet has a length different from another inlet. Additionally or alternatively, one of the inlets has the aperture oriented in a different direction from the aperture of the other inlet. Optionally, at least one of the inlets enters the airway tube from a direction different from the direction from which the other inlet enters the airway tube.

In accordance with some embodiments of the invention, there is provided a breath sampling method, comprising sampling breath from an airway tube through a sampling port comprising two or more inlets. The two or more inlets are connected to each other through a junction located outside of the air passageway of the airway tube. Optionally, the airway tube comprises an airway adapter.

In accordance with some embodiments of the invention, there is provided a breath sampling method, comprising sampling breath from an airway tube through a sampling port comprising two or more inlets. The two or more inlets are connected to each other through a junction located outside of the air passageway of the airway tube. In some embodiments of the invention a length of the inlet is substantially greater than a width of an aperture of the inlet. Additionally, the length of the inlet is shorter than a distance between two apertures of two adjacent inlets. Alternatively, the length of the inlet is substantially equal to the distance between two apertures of two adjacent inlets. Optionally, the inlet is narrowest at its respective aperture.

In accordance with some embodiments of the invention, there is provided a breath sampling method, comprising sampling breath from an airway tube through a sampling port comprising two or more inlets. The two or more inlets are connected to each other through a junction located outside of the air passageway of the airway tube. In some embodiments of the invention, the inlet has a length different from another inlet. Additionally or alternatively, one of the inlets has the aperture oriented in a different direction from the aperture of the other inlet. Optionally, at least one of the inlets enters the airway tube from a direction different from the direction from which the other inlet enters the airway tube.

BRIEF DESCRIPTION OF FIGURES

Examples illustrative of embodiments of the invention are described below with reference to figures attached hereto. In the figures, identical structures, elements or parts that appear in more than one figure are generally labeled with a same numeral in all the figures in which they appear. Dimensions of components and features shown in the figures are generally chosen for convenience and clarity of presentation and are not necessarily shown to scale. The figures are listed below.

DETAILED DESCRIPTION

Figure 1:
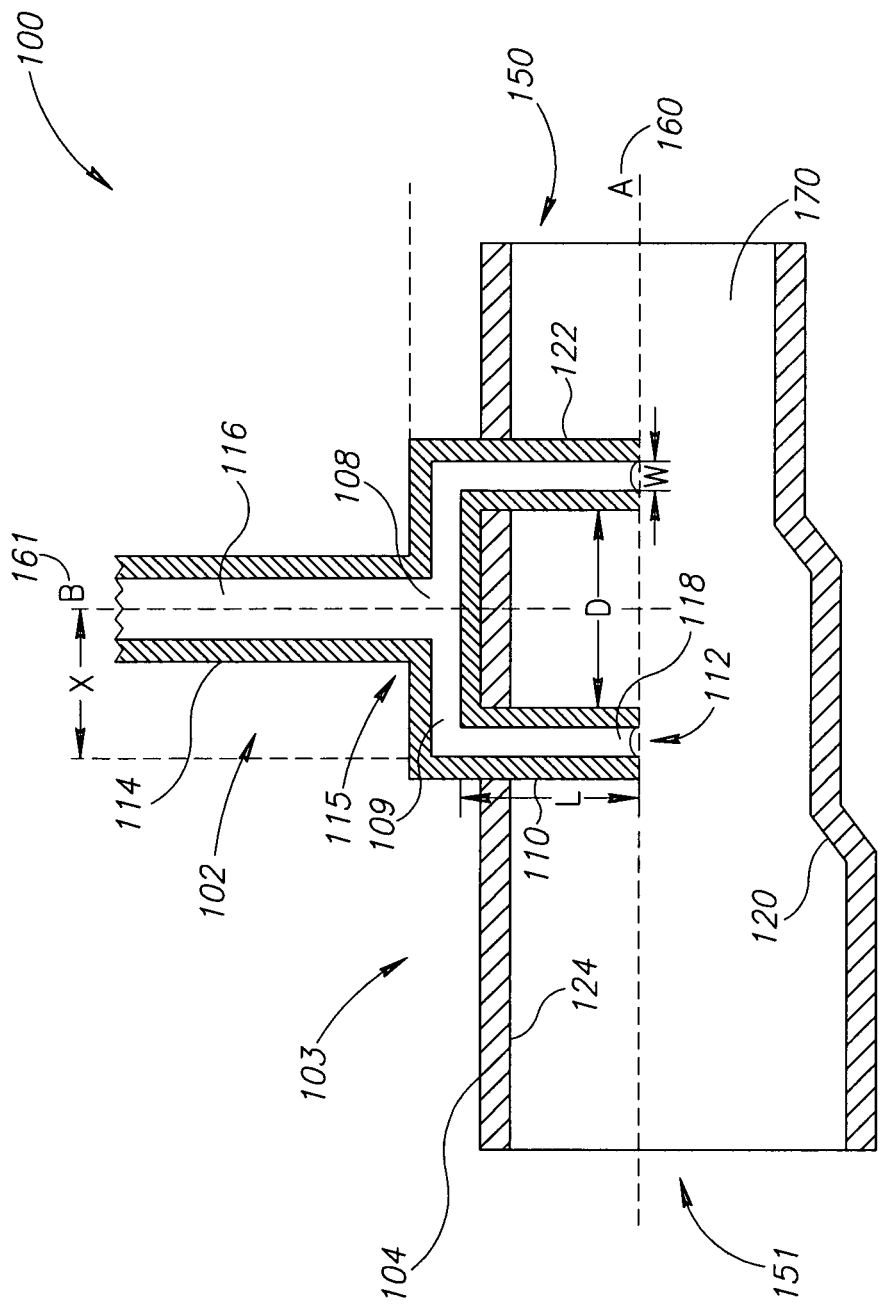
FIG. 1 schematically illustrates a cross sectional view of an exemplary airway adapter and an exemplary sampling port in accordance with an embodiment of the invention.

Reference is made to FIG. 1 which schematically illustrates a cross sectional view of an exemplary airway adapter 103 and an exemplary sampling port 102 in accordance with an embodiment of the invention. Sampling port 102 and an airway tube comprising airway adapter 103 are comprised in a breath sampling system 100. Airway adapter 103 is a tube with a substantially circular cross section, and comprises a circular outer wall 104 and a circular inner wall 124. At one end of adapter 103 is an opening 150 which connects, usually by means of appropriate fittings, to a patient's intubation tube (not shown). Opening 150 leads into an adapter passageway 170 through which exhaled breath flows from the patient into the patient airway tube (not shown) and through which air flows from the patient airway tube to the patient. At the other end of passageway 170 is opening 151 which generally connects to the patient airway tube. Opening 150 is typically of a smaller diameter than opening 151; the adjustment in the diameter of airway adapter 103 is done in two or more slanted steps, such as step 120. Optionally, the adjustment in the diameter may be done in one slanted step, or alternatively, as a sloping surface extending from one opening to the other. Optionally, in some embodiments of the invention, opening 150 and 151 are of the same diameter.

Positioned between openings 150 and 151 is sampling port 102. Sampling port 102 comprises an air collector 114, a channel 115, and two inlets such as, for example inlet 110 and inlet 122. The two inlets, inlet 110 and inlet 122 are connected to each other at a junction 108. Optionally, the sampling port may have more than two inlets, for example 3, 4, 5, 6 or more inlets. In case there are more than two inlets, such as 3, 4, 5, 6 or more inlets, at least two of the inlets and optionally more than two of the inlets are connected to each other at one junction, such as junction 108. The junction, such as junction 108, is adapted to allow airflow between the inlets, such as inlet 110 and inlet 122, and the channel 115. In function, when a liquid droplet reaches one inlet, such as inlet 110, and moves towards the airway tube, such as the airway adapter 103, it reaches the airway tube's, such as the airway adapter 103, inner wall, such as circular inner wall 124. When the liquid droplet reaches the inner wall, such as circular inner wall 124, it spreads thereon and thus no liquid, or at least a substantially reduced amount of liquid, reaches the second inlet, such as inlet 122. Of course, this description may be applicable for the progression of liquid from any inlet to any other inlet. This prevents or at least reduces the passage of liquid from one inlet to another and thus, if and when one inlet is blocked by liquid, the other inlet will remain open for airflow.

Air Collector 114 connects at one end to the inlets through channel 115 and is adapted to connect at the other end to a breath sampling tube (not shown). Collector 114 and channel 115 are tubes with substantially circular cross sections, and comprise collector bore 116, a channel bore 109, and the junction 108. Optionally, the channel may have other cross sections, for example rectangular or elliptical. The channel preferably forms a 90° angle with the air collector, resembling an inverted "T" with the channel and the air collector forming the head and the base of the "T", respectively. Collector bore 116 and channel bore 109 are of diameters which allow the exhaled breath samples to pass from the inlets, through the channel, meeting at the junction, and continuing on through the air collector, to the breath sampling tube without substantially affecting their waveform. The channel is positioned such that the junction is exteriorly located to the airway adapter, and abuts the outer circular wall, extending along a portion of the length of the adapter parallel to a central A axis 160. Central axis A 160 is an axis which extends along the length of passageway 170 and intersects the center of opening 150, and is substantially the center of the flow path of exhaled breath from the patient as it leaves the intubation tube.

The inlets generally perpendicularly extend from the channel through outer wall 104 and inner wall 124 of airway adapter 103 to the central axis A 160. Optionally, the inlets may slantedly extend from the channel in the direction of the central axis A, traversing the outer wall and the inner wall at an angle. Alternatively, the inlets may slantedly extend from the junction substantially eliminating the channel. The inlets are separated by a distance D one from the other and are typically symmetrically positioned about a central axis B 161 which extends along the length of collector bore 116. Optionally, the inlets may be asymmetrically positioned with respect to axis B 161. The inlets are tubes with substantially circular cross sections, although in other embodiments of the invention the inlets may have other cross sections, for example rectangular or elliptical. Each inlet comprises a bore, for example inlet bore 118, of diameter W. The bores, of inlet length L, extend from an aperture, such as aperture 112 in inlet 110, to intersect channel bore 109 in channel 115. The length of the inlet may be, according to some embodiments, substantially greater than the diameter, W, of the inlet bore, for example, $L \geq 4W$, 5W, 10W, 15W. Optionally, according to some embodiments, length $L \leq D$ where D is the distance between the inlets.

Figure 2:
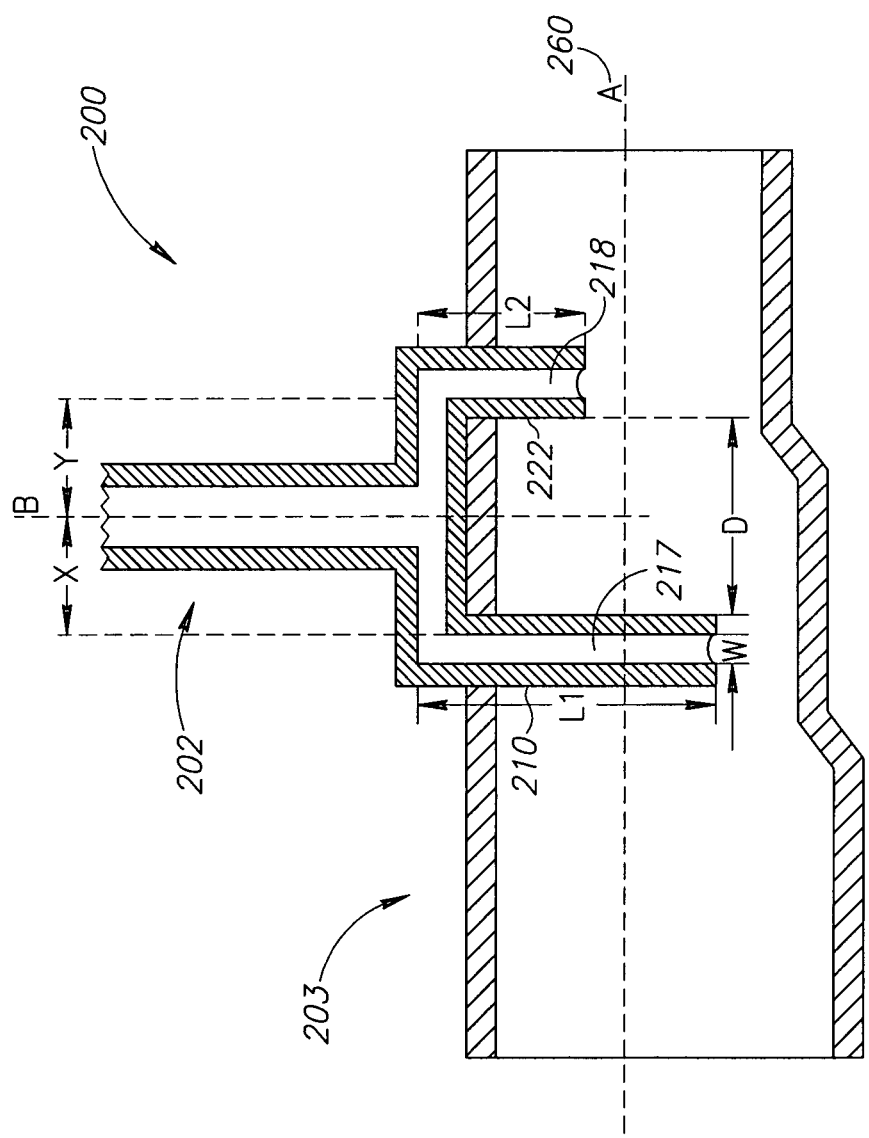
FIG. 2 schematically illustrates a cross-sectional view of an exemplary airway adapter and an exemplary sampling port in accordance with another embodiment of the invention.

Reference is made to FIG. 2 which schematically illustrates a cross sectional view of an exemplary airway adapter 203 and an exemplary sampling port 202 in accordance with another embodiment of the invention. Sampling port 202 and an airway tube comprising airway adapter 203 are comprised in a breath sampling system 200.

Airway adapter 203 is substantially similar to or the same as airway adapter 103 shown in FIG. 1. Sampling port 202 is substantially similar to sampling port 102 in FIG. 1 modified such that an inlet in FIG. 1 extends past a central axis A 260, shown as inlet 210, and a second inlet does not reach the central axis A 260, shown as inlet 222. Central axis A 260 is substantially similar to or the same as central axis A 160 in FIG. 1. In other embodiments of the invention, inlet 210 may not reach central axis A 260 while inlet 222 extends past central axis A 260. Optionally both inlets do not reach central axis A or, alternatively, both inlets may extend past central axis A.

The inlets comprise an inlet bore substantially similar to that of the inlets in FIG. 1, modified such that an inlet bore 217 comprised by inlet 210 is defined by an inlet length L1 while an inlet bore 218 comprised by inlet 222 is defined by an inlet length L2. The lengths of the inlets, L1 and L2 respectively, may be, according to some embodiments, substantially greater than the diameter, W of the inlet bores, for example, $L1 \geq 4W$, 5W, 10W, 15W and $L2 \geq 4W$, 5W, 10W, 15W. Optionally, according to some embodiments, length $L1 \leq D$ and $L2 \leq D$ where D is the distance between the inlets.

Figure 3:
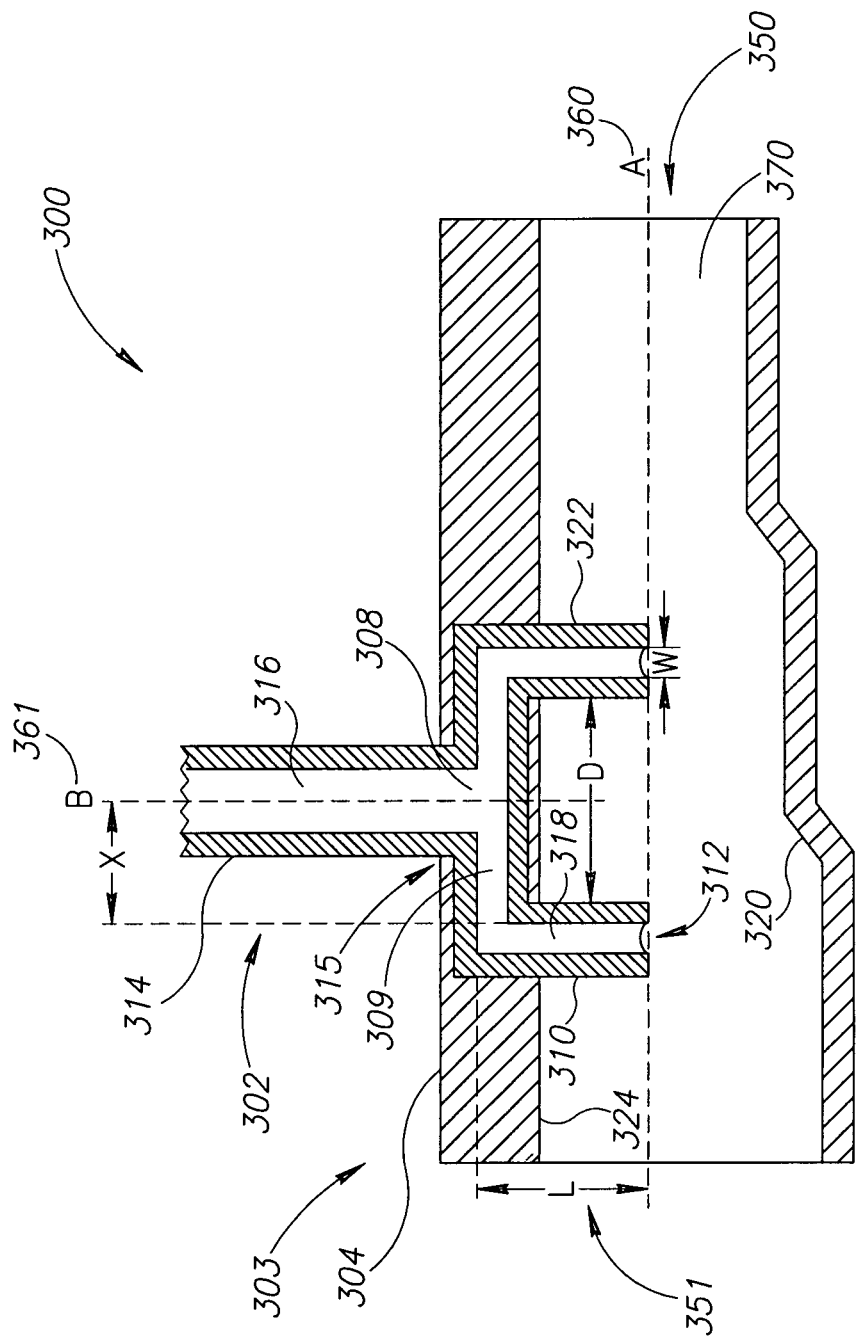
FIG. 3 schematically illustrates a cross-sectional view of an exemplary airway adapter and an exemplary sampling port in accordance with another embodiment of the invention.

Reference is made to FIG. 3 which schematically illustrates a cross sectional view of an exemplary airway adapter 303 and an exemplary sampling port 302 in accordance with another embodiment of the invention. Sampling port 302 and an airway tube comprising airway adapter 303 are comprised in a breath sampling system 300. Airway adapter 303 is a tube with a substantially circular cross section, and comprises a circular outer wall 304 and a circular inner wall 324. At one end of adapter 303 is an opening 350 which connects, usually by means of appropriate fittings, to a patient's intubation tube (not shown). Opening 350 leads into an adapter passageway 370 through which exhaled breath flows from the patient into the patient airway tube (not shown) and through which air flows from the patient airway tube to the patient. At the other end of passageway 370 is opening 351 which generally connects to the patient airway tube. Opening 350 is typically of a smaller diameter than opening 351; the adjustment in the diameter of airway adapter 303 is done in two or more slanted steps, such as step 320. Optionally, the adjustment in the diameter may be done in one slanted step, or alternatively, as a sloping surface extending from one opening to the other. Optionally, in some embodiments of the invention, opening 350 and 351 are of the same diameter.

Positioned between openings 350 and 351 is sampling port 302. Sampling port 302 comprises an air collector 314, a channel 315, and two inlets such as, for example inlet 310 and inlet 322. The two inlets, inlet 310 and inlet 322 are connected to each other at a junction 308. Optionally, the sampling port may have more than two inlets, for example 3, 4, 5, 6 or more inlets. In case there are more than two inlets, such as 3, 4, 5, 6 or more inlets, at least two of the inlets and optionally more than two of the inlets are connected to each other at one junction, such as junction 308. The junction, such as junction 308, is adapted to allow airflow between the inlets, such as inlet 310 and inlet 322, and the channel 315. In function, when a liquid droplet reaches one inlet, such as inlet 310, and moves towards the airway tube, such as the airway adapter 303, it reaches the airway tube's, such as the airway adapter 303, inner wall, such as circular inner wall 324. When the liquid droplet reaches the inner wall, such as circular inner wall 324, it spreads thereon and thus no liquid, or at least a substantially reduced amount of liquid, reaches the second inlet, such as inlet 322. Of course, this description may be applicable for the progression of liquid from any inlet to any other inlet. This prevents or at least reduces the passage of liquid from one inlet to another and thus, if and when one inlet is blocked by liquid, the other inlet will remain open for airflow.

Air Collector 314 connects at one end to the inlets through channel 315 and is adapted to connect at the other end to a breath sampling tube (not shown). Collector 314 and channel 315 are tubes with substantially circular cross sections, and comprise collector bore 316, channel bore 309, and junction 308. Optionally, the channel may have other cross sections, for example rectangular or elliptical. The channel preferably forms a 90° angle with the air collector, resembling an inverted "T" with the channel and the air collector forming the head and the base of the "T", respectively. Collector bore 316 and channel bore 309 are of diameters which allow the exhaled breath samples to pass from the inlets, through the channel, meeting at the junction, and continuing on through the air collector, to the breath sampling tube without substantially affecting their waveform. The channel is positioned such that the junction lies embedded between the outer circular wall and the inner circular wall of the airway adapter, and extends along a portion of the length of the adapter parallel to a central A axis 360. Optionally, the channel may lie such that it is partially outside the outer circular wall. Central axis A 360 is an axis which extends along the length of passageway 370 and intersects the center of opening 350, and is substantially the center of the flow path of exhaled breath from the patient as it leaves the intubation tube.

The inlets generally perpendicularly extend from the channel through inner wall 324 of airway adapter 303 to the central axis A 360. Optionally, the inlets may slantedly extend from the channel through the inner wall in the direction of the central axis A, traversing the inner wall at an angle. Alternatively, the inlets may slantedly extend from the junction substantially eliminating the channel. The inlets are separated by a distance D one from the other and are typically symmetrically positioned about a central axis B 361 which extends along the length of collector bore 316. Optionally, the inlets may be asymmetrically positioned with respect to axis B 361. The inlets are tubes with substantially circular cross sections, although in other embodiments of the invention the inlets may have other cross sections, for example rectangular or elliptical. Each inlet comprises a bore, for example inlet bore 318, of diameter W. The inlet bores, of inlet length L, extend from an aperture, such as aperture 312 in inlet 310, to intersect channel bore 309 in channel 315. The length of the inlet may be, according to some embodiments, substantially greater than the diameter, W, of the inlet bore, for example, $L \geq 4W$, 5W, 10W, 15W. Optionally, according to some embodiments, length $L \leq D$ where D is the distance between the inlets.

Figure 4:
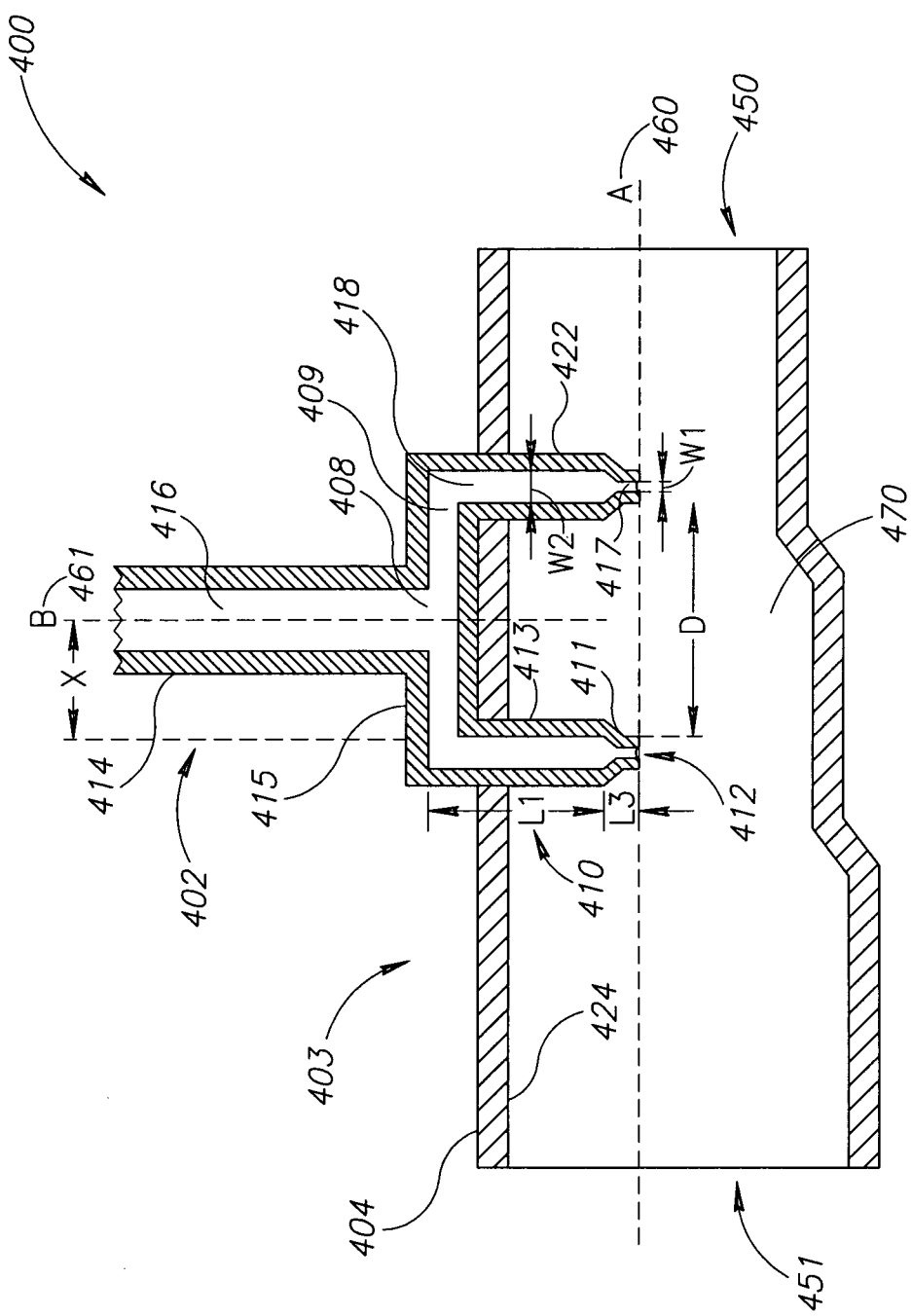
FIG. 4 schematically illustrates a cross-sectional view of an airway adapter and a sampling port with reduced aperture diameter in accordance with another embodiment of the invention.

Reference is made to FIG. 4 which schematically illustrates a cross sectional view of an exemplary airway adapter 403 and an exemplary sampling port 402 comprising inlets with reduced aperture size in accordance with another embodiment of the invention. Sampling port 402 and an airway tube comprising airway adapter 403 are comprised in a breath sampling system 400. Airway adapter 403 is substantially similar to or the same as airway adapter 103 shown in FIG. 1.

Positioned between openings 450 and 451 is sampling port 402. Sampling port 402 comprises an air collector 414, a channel 415, and two inlets such as, for example inlet 410 and inlet 422. The two inlets, inlet 410 and inlet 422 are connected to each other at a junction 408. Optionally, the sampling port may have more than two inlets, for example 3, 4, 5, 6 or more inlets. In case there are more than two inlets, such as 3, 4, 5, 6 or more inlets, at least two of the inlets and optionally more than two of the inlets are connected to each other at one junction, such as junction 408. The junction, such as junction 408, is adapted to allow airflow between the inlets, such as inlet 410 and inlet 422, and the channel 415. In function, when a liquid droplet reaches one inlet, such as inlet 410, and moves towards the airway tube, such as the airway adapter 403, it reaches the airway tube's, such as the airway adapter 403, inner wall, such as circular inner wall 424. When the liquid droplet reaches the inner wall, such as circular inner wall 424, it spreads thereon and thus no liquid, or at least a substantially reduced amount of liquid, reaches the second inlet, such as inlet 422. Of course, this description may be applicable for the progression of liquid from any inlet to any other inlet. This prevents or at least reduces the passage of liquid from one inlet to another and thus if and when one inlet is blocked by liquid the other inlet will remain open for airflow.

Air Collector 414 connects at one end to the inlets through channel 415 and is adapted to connect at the other end (not shown) to a breath sampling tube (not shown). Collector 414 and channel 415 are tubes with substantially circular cross sections, and comprise collector bore 416 a channel bore 409, and the junction 408. Optionally, the channel may have other cross sections, for example rectangular or elliptical. The channel preferably forms a 90° angle with the air collector, resembling an inverted "T" with the channel and the air collector forming the head and the base of the "T", respectively. Collector bore 416 and channel bore 408 are of diameters which allow the exhaled breath samples to pass from the inlets, through the channel, meeting at the junction, and continuing on through the air collector, to the breath sampling tube without substantially affecting their waveform. The channel is positioned such that the junction is exteriorly located to the airway adapter, and abuts the outer circular wall, extending along a portion of the length of the adapter parallel to a central A axis 460. Central axis A 460 is an axis which extends along the length of passageway 470 and intersects the center of opening 450, and is substantially the center of the flow path of exhaled breath from the patient as it leaves the intubation tube.

The inlets generally perpendicularly extend from the channel through outer wall 404 and inner wall 424 of airway adapter 403 to the central axis A 460. Optionally, the inlets may slantedly extend from the channel in the direction of the central axis A, traversing the outer wall and the inner wall at an angle. Alternatively, the inlets may slantedly extend from the junction substantially eliminating the channel. The inlets are separated by a distance D one from the other and are typically symmetrically positioned about a central axis B 461 which extends along the length of collector bore 416. Optionally, the inlets may be asymmetrically positioned with respect to axis B 461. The inlets are tubes with substantially circular cross sections and comprise an inlet section which connects with channel 415 at one end, such as inlet section 413, and an end section, such as end section 411. Optionally, the inlets may have other cross sections, for example rectangular or elliptical.

Each inlet comprises a bore, for example bore 418, which extends a length L1 of the insert section and a substantially narrower bore, for example bore 417, which extends a length L3 of the end section and terminates at an aperture 412. The cross-sectional diameter of bore 418, W2, and of bore 417, W1, and the transition between the bores, shall be such that the waveform of the exhaled breath samples is not affected when passing through the bores. The length of the inlet section, L1, may be, according to some embodiments, substantially greater than the diameter, W2, for example, $L \geq 4W_2$, $5W_2$, $10W_2$, $15W_2$. Optionally, according to some embodiments, length $L1+L3 \leq D$ where D is the distance between the apertures of the inlets and L3 is the length of the end section.

Figure 5:
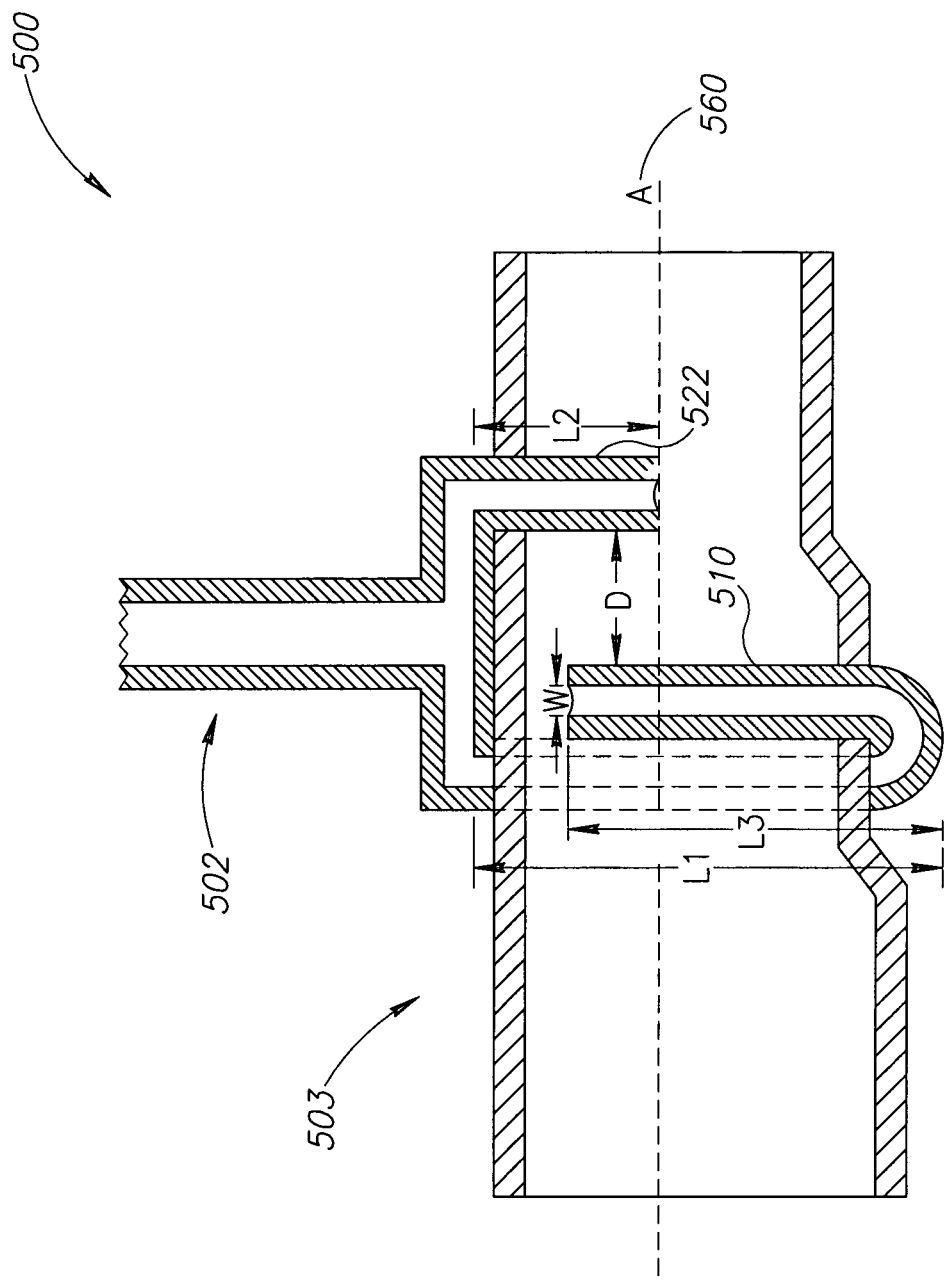
FIG. 5 schematically illustrates a cross-sectional view of an airway adapter and a sampling port comprising inlets extending into the airway tube from different directions in accordance with another embodiment of the invention.

Reference is made to FIG. 5 which schematically illustrates a cross sectional view of an exemplary airway adapter 503 and an exemplary sampling port 502 in accordance with another embodiment of the invention. Sampling port 502 and an airway tube comprising airway adapter 503 are comprised in a breath sampling system 500.

Airway adapter 503 is substantially similar to or the same as airway adapter 103 shown in FIG. 1. Sampling port 502 is substantially similar to sampling port 102 in FIG. 1 modified such that an inlet extends past a central axis A 560, shown as inlet 522 and a second inlet enters airway adapter 503 from an opposing direction to that in which inlet 522 enters the airway adapter, and extends past central axis A 560, shown as inlet 510. Central axis A 560 is substantially similar to or the same as central axis A 160 in FIG. 1. In other embodiments of the invention, inlet 510 and inlet 522 may not reach central axis A 560, while in some other embodiments of the invention one inlet does not reach central axis A while the other extends past central axis A. Furthermore, in other embodiments of the invention, the two inlets may enter the airway adapter from any direction, for example, perpendicularly to one another, or at oblique angles relative to one another, or at obtuse angles relative to one another.

The inlets comprise an inlet bore substantially similar to that of the inlets in FIG. 1 modified such that the inlet bore comprised by inlet 510 is defined by an inlet length L1+L3 while the inlet bore comprised by inlet 522 is defined by an inlet length L2. The lengths of the inlets, L1+L3 and L2 respectively, may be, according to some embodiments, substantially greater than the diameter, W of the inlet bores, for example, $L1+L3 \geq 4W$, 5W, 10W, 15W and $L2 \geq 4W$, 5W, 10W, 15W. Optionally, according to some embodiments, length $L1+L3 \leq D$ and $L2 \leq D$ where D is the distance between the inlets.

In accordance with an embodiment of the invention, the diameter of the inlet bore is preferably in the range of 0.5 mm-1 mm, for example 0.6 mm; the diameters of the channel bore and the air collector bore are preferably in the range of 0.5 mm-2 mm, for example 1 mm. The combined length of the channel and the inlets is preferably in the range of 10 mm-22 mm, for example 15 mm, assuming that the aperture is in the proximity of the central axis A of the airway adapter.

Although the drawings refer to various embodiments of airway adapters, the structures and functions described herein also apply to any airway tube or a portion of an airway tube which are thus covered under the scope of this disclosure.

While a number of exemplary aspects and embodiments have been discussed above, those of skill in the art will recognize certain modifications, permutations, additions and sub-combinations thereof. It is therefore intended that the following appended claims and claims hereafter introduced be interpreted to include all such modifications, permutations, additions and sub-combinations as are within their true spirit and scope.

What we claim is:

1. An apparatus for exhaled breath sampling, comprising:
a substantially tubular airway adapter having an outer wall and an interior space, the outer wall having an interior surface and an exterior surface; and
a breath sampling port comprising:
a breath collector extending outside of the outer wall of the airway adapter, the breath collector being substantially perpendicular to the interior surface of the airway adapter;
two or more inlets, each of the inlets extending through at least the interior surface of the outer wall of the substantially tubular airway adapter and into the interior space of the airway adapter, and being in fluid communication with any gas within the interior space of the airway adapter, and
a channel extending between the two or more inlets, the channel located externally to at least the interior surface of the substantially tubular airway adapter and being substantially perpendicular to a wall of the breath collector and to the inlets;
wherein the two or more inlets each comprise a bore extending from an inlet opening at the end that extends into the interior space of the airway adapter to a channel opening, at an opposite end of the inlet, extending into the channel, wherein a distance between each of the channel openings and the junction is substantially greater than a diameter of the inlet bore, thereby substantially preventing liquids blocking a first of the inlets to migrate to a second of the inlets; and wherein the opposite ends of the inlets are connected to each other at a junction located within the channel and externally to the interior surface of the outer wall of the airway adapter.

2. The apparatus of claim 1, wherein the apparatus is configured to substantially reduce passage of liquid from one of the inlets to another.

3. The apparatus of claim 1, wherein the channel is located outside the outer wall of the airway adapter and wherein the junction substantially abuts the outer wall.

4. The apparatus of claim 1, wherein the channel is embedded between the interior and exterior surfaces of the outer wall of the airway adapter.

5. The apparatus of claim 1, wherein the channel is at least partially embedded between the interior and exterior surfaces of the outer wall of the airway adapter.

6. The apparatus of claim 1, wherein a length of each of the two or more inlets is shorter than the distance between the channel openings, thereby preventing liquids from entering into the inlet bore.

7. The apparatus of claim 1, wherein the bore of the two or more inlets are narrowest at each of their respective inlet opening.

8. The apparatus of claim 1, wherein at least one of the inlets has a length between the inlet opening thereof and the junction different from the length between the inlet opening of another inlet and the junction.

9. The apparatus of claim 1, wherein at least one of the inlets has an inlet opening oriented in a different direction than the inlet opening of another inlet.

10. The apparatus of claim 1, wherein at least one of the inlets enters the airway adapter from a direction different than the direction from which another of the inlets enters the airway adapter.

11. A breath sampling method using an apparatus of claim 1, comprising:
    causing exhaled breath to pass through the airway adapter;
    sampling exhaled breath from the airway adapter through the breath sampling port.

12. The apparatus of claim 1, wherein the two or more inlets are substantially parallel.

* * * * *